United States Patent
Bacher et al.

(10) Patent No.: US 10,045,762 B2
(45) Date of Patent: Aug. 14, 2018

(54) DILATION DEVICE AND EXPANDABLE COVERING FOR A DILATION INSTRUMENT

(71) Applicant: Karl Storz SE & Co. KG, Tuttlingen (DE)

(72) Inventors: Uwe Bacher, Tuttlingen (DE); Martin Blocher, Stockach-Espasingen (DE); Jochen Schmidberger, Schoemberg (DE); Tobias Unger, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 250 days.

(21) Appl. No.: 14/273,290

(22) Filed: May 8, 2014

(65) Prior Publication Data

US 2014/0336688 A1    Nov. 13, 2014

(30) Foreign Application Priority Data

May 8, 2013    (DE) .......................... 10 2013 104 789

(51) Int. Cl.
*A61M 29/00*    (2006.01)
*A61B 17/00*    (2006.01)
(Continued)

(52) U.S. Cl.
CPC .... *A61B 17/00234* (2013.01); *A61B 1/00112* (2013.01); *A61B 1/32* (2013.01);
(Continued)

(58) Field of Classification Search
CPC ............ A61B 19/081; A61B 2019/083; A61B 1/00112; A61B 1/00128; A61B 1/00135; A61B 1/32; A61B 2017/320044; A61B 17/29; A61B 2050/0063; A61M 29/00; A61M 39/10; A61M 2039/1033
See application file for complete search history.

(56) References Cited

U.S. PATENT DOCUMENTS

| 1,271,456 | A | * | 7/1918 | Flack | .................... | A61F 5/0093 |
| | | | | | | 606/197 |
| 4,320,762 | A | * | 3/1982 | Bentov | ................. | A61M 29/02 |
| | | | | | | 606/198 |

(Continued)

FOREIGN PATENT DOCUMENTS

| DE | 3935579 A1 | 5/1991 |
| DE | 29607043 U1 | 8/1996 |

(Continued)

*Primary Examiner* — Katherine Rodjom
(74) *Attorney, Agent, or Firm* — Whitmyer IP Group LLC

(57) ABSTRACT

A dilation device including a dilation instrument which includes a distal radially expandable section which is coupled via an elongate shank to a handling section, and an expandable covering with a closed distal end and an open proximal end, for the expansion section of the dilation instrument. The covering has a shank section extending along the shank of the dilation instrument. The open proximal end of the covering is detachably coupled to the distal end of the handling section of the dilation instrument. Furthermore, the covering is disclosed per se, which consists of a mesh material and has a shank section, which is connected to a coupling sleeve at the open proximal end.

19 Claims, 12 Drawing Sheets

(51) Int. Cl.
*A61B 1/00* (2006.01)
*A61B 1/32* (2006.01)
*A61B 17/24* (2006.01)
*A61B 46/17* (2016.01)
*A61B 46/10* (2016.01)

(52) U.S. Cl.
CPC .............. *A61B 17/24* (2013.01); *A61B 46/10* (2016.02); *A61B 46/17* (2016.02); *A61M 29/00* (2013.01)

(56) References Cited

U.S. PATENT DOCUMENTS

| | | | | |
|---|---|---|---|---|
| 4,744,363 | A * | 5/1988 | Hasson | A61B 17/0218 606/1 |
| 5,078,681 | A | 1/1992 | Kawashima | |
| 5,178,133 | A * | 1/1993 | Pena | A61B 17/0218 600/203 |
| 5,197,971 | A * | 3/1993 | Bonutti | A61B 17/0218 604/105 |
| 5,672,158 | A * | 9/1997 | Okada | A61M 25/0014 604/164.1 |
| 6,126,359 | A * | 10/2000 | Dittrich | A61B 17/29 403/325 |
| 2005/0203565 | A1* | 9/2005 | Rethy | A61B 17/3403 606/198 |
| 2010/0283238 | A1* | 11/2010 | Deighan | A61M 39/10 285/328 |
| 2013/0053863 | A1* | 2/2013 | Juravic | A61B 1/303 606/119 |
| 2014/0128870 | A1* | 5/2014 | Brenzel | A61B 17/7225 606/62 |

FOREIGN PATENT DOCUMENTS

| | | |
|---|---|---|
| DE | 69626574 T2 | 4/2004 |
| DE | 69819489 T2 | 9/2004 |
| DE | 102009058132 A1 | 6/2011 |
| EP | 0331040 A1 | 9/1989 |
| EP | 2412315 A2 | 2/2012 |

* cited by examiner

DILATION DEVICE AND EXPANDABLE COVERING FOR A DILATION INSTRUMENT

FIELD OF THE INVENTION

The present invention relates to a covering for a dilation tool and to a dilation instrument.

BACKGROUND OF THE INVENTION

Dilation instruments are used, inter alia, in endoscopic ENT surgery, but also in other specialist areas of medicine. They are used to remove pathological stenoses by virtue of an expandable section being introduced into the region of the stenosis and the section being dilated. A simple solution for dilation lies in use of a balloon catheter which is disadvantageous if the balloon bursts and "pumping work" is required by the operator if a gas is used. If use is made of an incompressible fluid, the biocompatibility thereof, in turn, needs to be taken into account. Purely mechanical dilation instruments are also known; although these usually cannot be dilated in an ideal manner, they do permit sensitive force feedback with fewer hand movements. Mechanical dilation instruments are often disadvantageous in that comparatively large gaps are formed between the spreading jaws in the spread state, which contributes to an increased risk of trauma due to a pressure load which is too high and due to clamping. As a result of this, overcoats were developed for mechanical dilation instruments, which overcoats are intended to compensate these gaps, homogenize the introduction of force into the tissue and prevent the ingress of tissue into the dilation mechanism.

A dilation instrument with such an overcoat and a method and a device for applying the overcoat have been disclosed in EP 2 412 315 A2. There, the overcoat is held in the device and dilated at the proximal end of said overcoat. The device has a conical insertion aid for the expandable end of the dilation instrument such that it can be introduced into the overcoat more easily. There, the overcoat merely extends over the expandable section in which the dilation mechanism is also arranged. When the dilation mechanism is actuated, the overcoat may inadvertently slip off the expandable end.

SUMMARY OF THE INVENTION

This object is achieved by a dilation device having the features of the invention.

Moreover, a further object which emerges lies in developing an expandable covering for the expansion section of a dilation instrument, which covering can be coupled quickly and without an aid device to the dilation instrument, and can be produced in a cost-effective manner.

This object is achieved by an expandable covering for the expansion section of a dilation instrument, having the features of the invention.

In accordance with a first embodiment, the dilation device according to the invention comprises a dilation instrument which comprises a distal radially expandable section which is coupled via an elongate shank to a handling section, and an expandable covering, with a closed distal end and an open proximal end, for the expansion section of the dilation instrument. The covering has a shank section extending along the shank of the dilation instrument. The open proximal end of the covering is detachably coupled to a distal end of the handling section of the dilation instrument.

Herein, proximal and distal are to be understood in relation to a person using the dilation device. Accordingly, proximal is a position situated close to this person and distal is a position situated away from the person.

The covering extending over a majority of the length of the shank of the dilation instrument, or even over the whole length thereof, is advantageous over known coverings which are only pulled over the expansion section: thus, the covering cannot inadvertently slip off, even in the case of great expansion of the expansion section; there may also be longitudinal stretching, but the covering is securely fastened to the handling section. The radial expandability or elasticity of the covering in the expansion section should be dimensioned at least in such a way that it can follow the expansion of the dilation instrument without damage; a safety reserve can also be provided therefor.

Therefore, the covering can advantageously be a disposable covering; however, multiple possible use of the covering is not precluded, which may be expedient, in particular, if use is made of precious substances. The covering can be indirectly or directly coupled to the handling section of the dilation instrument; by way of example, a direct connection can be achieved by virtue of the covering being inserted into a coupling device on the handling section, for example a type of tensioning ring or tensioning hook. Indirect coupling can be achieved by virtue of the covering being connected to an intermediate element for coupling purposes, for example a nut or a quick release element, and the latter then being coupled to the handling section.

In principle, the dilation device according to the invention can be operated with mechanical, hydraulic, pneumatic or electric dilation instruments. Furthermore, the covering is not restricted to specific shank diameters, shank lengths or diameters of the expansion section of the dilation instrument.

In a further embodiment, the covering can consist of a mesh material, for example of a wire mesh material which can advantageously be made from a biocompatible stainless steel.

In the case of a mesh material, the expansion of the covering can be achieved not only by elastic stretching of the wires, but also—and by using significantly less force—by mutual sliding or displacement of the wires. The aforementioned substances are not to be understood in a restrictive sense. Further substances for the mesh material are conceivable, for example polymers.

In a yet further embodiment, the shank section of the covering can be connected to a coupling sleeve, in particular adhesively bonded to the coupling sleeve, at the open proximal end. Additionally, a coupling device can be connected, in particular detachably connected and particularly advantageously connected via a thread, to the far end of the handling section of the dilation instrument. Here, the coupling sleeve of the covering can be detachably coupled to the coupling device of the dilation instrument.

This embodiment is an instance of indirect coupling since, on part of the covering, the coupling sleeve has been "interposed" and, on part of the dilation instrument, the coupling device has been "interposed". Using this type of coupling, the covering can be coupled significantly more quickly to the dilation instrument, and decoupled therefrom, than in the case of direct coupling. An advantage of indirect coupling is that the coupling and decoupling state are explicitly predetermined; the coupling sleeve and coupling device can only be brought into engagement in a predetermined manner. In the case of direct coupling, the covering is hooked into the tensioning device, for example a collet, a tensioning ring or a tensioning hook, with there being the risk of user errors during the coupling, which could ultimately lead to inadvertent detachment of the covering. The covering can be pulled over the coupling sleeve, adhesively bonded to the outer lateral face of the coupling sleeve or else be held additionally with interlocking holding means, such as hooks which correspond to the structural dimensions of the covering. The coupling device can particularly advantageously have the same external cross-sectional shape and the same dimensions as the handling section of the dilation instrument, and so the coupling device is inserted harmoniously into the general view of the instrument and does not cause bothersome transitions from an ergonomic standpoint either.

Moreover, the coupling sleeve can comprise a bayonet closure element, which in particular can comprise a substantially L-shaped insertion recess extending from a proximal end face of the coupling sleeve in a longitudinal axial manner in the wall of the coupling sleeve. There can be a locking recess at the closed end of the L-shaped insertion recess. Additionally, the coupling device can comprise at least one radially inwardly extending locking lug, the dimensions of which correspond to the insertion recess of the coupling sleeve. In the locked state, the locking lug of the coupling device is held by the locking recess of the coupling sleeve.

In this embodiment, the coupling sleeve and the coupling device form a bayonet closure, which naturally can also be transferred into an open state. As is also the case in the case of bayonet closures with an L-shaped insertion recess or guide groove, the coupling sleeve is moved in a longitudinal axial manner in order to overcome the engagement with the locking recess and in order then to be threaded out of the insertion recess by rotation followed by a longitudinal axial displacement. Advantageously, the coupling sleeve can consist of an injection-moldable plastic since this also allows complex geometries to be produced at reasonable costs. However, this does not preclude the possibility of other substances such as metals or ceramics being used, for example if increased demands on hygiene or a higher resistance to wear-and-tear are desired. The necessary longitudinal axial pretensioning force of the coupling sleeve, which presses the locking lug into the locking recess, can advantageously be generated by the covering itself, for example by virtue of the covering being slightly too short in the non-expanded state for being pulled over the shank and only being able to be brought into engagement with the insertion recess by a slight longitudinal axial rotation. In this case, it may advantageously be possible for the coupling sleeve to have a two-part embodiment: by way of example, it can consist of a rotatable inner sleeve, which can be brought into engagement with the coupling device, and an outer sleeve connected in a rotationally secured manner to the tube-like shank since this can prevent the tube-like shank from also being rotated when the bayonet closure is actuated.

Furthermore, a spring element can be arranged between a proximal end face of the coupling sleeve and a distal end face of the coupling device, with a compression spring being advantageous and a polymer disk, such as an O-ring, being particularly suitable.

The bayonet closure can be secured by applying the spring element without having to apply tension to the whole covering; this reduces the load on the covering. If, in order to close the bayonet closure, the locking lug is moved through the insertion recess to the locking recess, the spring element is reversibly compressed and partly relieved again when the locking lug is latched into the locking recess, wherein there still must be so much pretension that the locking lug can be held securely.

Moreover, the coupling device can comprise a holding space for the coupling sleeve of the covering, which holding space extends in a longitudinal axial manner from a distal end face of the coupling device in the direction of the proximal end thereof. The coupling sleeve is held therein, at least along the proximal end section thereof. Furthermore, a support end face, on which the coupling sleeve is supported, can adjoin the holding space in the proximal direction.

The coupling sleeve at least in part being held by the coupling device prevents blood, tissue or other dirt from entering the coupling sleeve and blocking the function thereof, while the covering stripped over the sleeve prevents the ingress of such substances from the distal end.

In accordance with a further embodiment, at least one radially outwardly extending assembly recess can be present on the coupling device, adjacent in the circumferential direction to the locking lug, wherein, in particular, there can be two assembly recesses on both sides of the locking lug. Alternatively or additionally, the coupling device can have an insertion chamfer at the distal end of the holding space.

The insertion chamfer is intended to simplify the introduction of the coupling sleeve into the holding space of the coupling device by virtue of the opening space "dilating" in the distal direction. Therefore, the user does not need to be as attentive during coupling; more attention can therefore be placed on other activities. Moreover, the coupling is accelerated since it is possible to prevent the coupling sleeve from jamming against flanges or projections. The assembly recesses serve for a simplified assembly and disassembly of the coupling device on the dilation tool, for example if the latter needs to be cleaned. By using a special tool, which corresponds to the assembly recesses, it is possible to tighten the coupling device with sufficiently high torque and release it again without much effort.

The expandable covering for a distal expansion section of a dilation instrument has a closed far end and an open near end in a first embodiment and consists of a mesh material. The open near end is connected to a coupling sleeve.

Although, in principle, the proximal and distal designations in relation to the covering are not absolutely necessary, they are nevertheless used because the covering is always pulled over a dilation instrument for use and the reference can therefore be established in an improved manner. The covering according to the invention, which consists of a mesh material and comprises a proximal coupling sleeve, can be coupled more quickly to a dilation instrument than known coverings made of silicone, the assembly of which always required an aid for threading-in or patience. According to the invention, the covering on the coupling device can also be gripped well with gloves and can be pulled over the shank of the dilation instrument without problems. Moreover, the covering according to the invention is more robust; the risk of damaging the covering as a result of contact with other sharp instruments or by the spreading jaws of the dilation instrument itself is significantly reduced. The mesh material can advantageously consist of a hard niro-wire (1.4401) with a diameter of 0.08 mm and have a high density or low mesh size such that as little blood, tissue and other dirt as possible can enter. By way of example, the high density (cover) can be 80% and be achieved by 48 individual wires, of which three wires are always wound to form a bundle. The diameter of the covering can advantageously be 2.5 to 10 mm.

In a further embodiment, the coupling sleeve can be longitudinally axially elastic in the proximal end section thereof, wherein the elasticity is advantageously achieved by an at least partly circumferential slit.

By slitting the proximal end section, a structure-integrated elasticity is, as it were, provided and can be used for pretensioning the bayonet closure. If the covering from this embodiment is used in a dilation device according to the invention, the additional resilient element can be dispensed with and the length of the covering can also be selected accordingly. Advantageously, such as slitted coupling sleeve can be produced in a cost-effective manner from an injection-moldable plastic.

In the proximal end section, the coupling sleeve can also comprise a plurality of parallel slits aligned normally with respect to the longitudinal axis. Webs are between the slits, which webs, in a developed view, advantageously extend in an alternating, wave-shaped or rectangular function-like manner. It is particularly advantageous if the coupling sleeve has two or more ring sectors, wherein the webs are arranged in a mirror-imaged fashion in respective neighboring ring sectors.

Here, the term ring sector should denote part of the coupling sleeve which is formed by a predetermined cross-sectional region extending along the longitudinal axis. The coupling sleeve will advantageously have an integer number of ring sectors, for example four pieces. Then, in two neighboring "longitudinal quarters", the webs—and also the slits—within each would be a mirror image of those in the other longitudinal quarter. By arranging a plurality of parallel slits, the elasticity achievable in a longitudinal section, and hence also the "tensioning path", can be increased. When this embodiment is used, a bayonet closure can be formed particularly well with the coupling device of a dilation instrument without further measures for longitudinal axial pretensioning needing to be made.

Furthermore, a grip aid sleeve advantageously with a spanner engagement portion or knurling can be arranged over a distal end section of the coupling sleeve. The grip aid sleeve is connected in a rotationally secured manner, and preferably adhesively bonded, to the distal end section.

The grip aid sleeve serves for simplifying handling of the covering, in particular when coupling with, and decoupling from, the dilation instrument, and for making it more ergonomic. Moreover, the grip aid sleeve covers the part of the mesh-like covering which is pulled over the coupling sleeve, and so it is optically more appealing on the one side and the fastening of the covering on the coupling sleeve is additionally protected on the other side since the mesh is situated in a ring gap between the coupling sleeve and the grip aid sleeve.

Furthermore, the coupling sleeve can have one or more latching recesses in the wall thereof, and the grip aid sleeve can have latching lugs corresponding thereto. The latching lugs of the grip aid sleeve in this case engage with the latching recesses of the coupling sleeve, as a result of which, in addition to adhesively bonding the mesh material in the ring gap between coupling sleeve and coupling device, the mesh material can also be held by an interlocking portion. By way of example, this interlocking portion can be formed by an adhesive which flowed into the recesses during adhesive bonding.

Moreover, an end sleeve, which is preferably crimped, welded, soldered and/or adhesively bonded to the distal end, is arranged over the distal closed end of the covering. As a result, the covering with the closed end can be produced cost-effectively and quickly from a tube manufactured in an open manner. Here, use can be made of sleeves similar to wire end ferrules known from electrical engineering. Alternatively, the distal end can also be formed from braid and soft solder and a dedicated end ferrule can be dispensed with. If a plastic is used as fabric, it can be heated and formed to make a distal closure.

Finally, the mesh material can be a knit or braid. The substance of the mesh material can be a metal or a metal alloy, with a biocompatible stainless steel or a shape memory alloy being advantageous. Alternatively, spring-tempered polymers, for example polyesters with medical approval, may be used as the substance.

The covering can be made in a simple and cost-effective manner using manufacturing technology from the textile sector and/or fiber-composite sector. However, it is also feasible to produce the covering by micro-machining processes or by laser cutting. In addition to stainless steels, there are also nickel titanium alloys which have excellent biocompatibility, for example shape memory alloys with very high elastic stretching and good dynamic or vibration load capacities, as are used in e.g. stents. From stent production, production methods which render it possible to produce flexible metal tubes with a diameter of less than one millimeter are also known.

These and further advantages are presented by the following description, with reference being made to the attached drawings.

BRIEF DESCRIPTION OF THE DRAWINGS

The reference to the figures in the description serves for assisting with the description and for simplified understanding of the subject matter. Objects or parts of objects which are substantially equal or similar can be provided with the same reference signs. The figures are merely schematic illustrations of exemplary embodiments of the invention.

In detail.

DETAILED DESCRIPTION OF THE INVENTION

Figure 1:
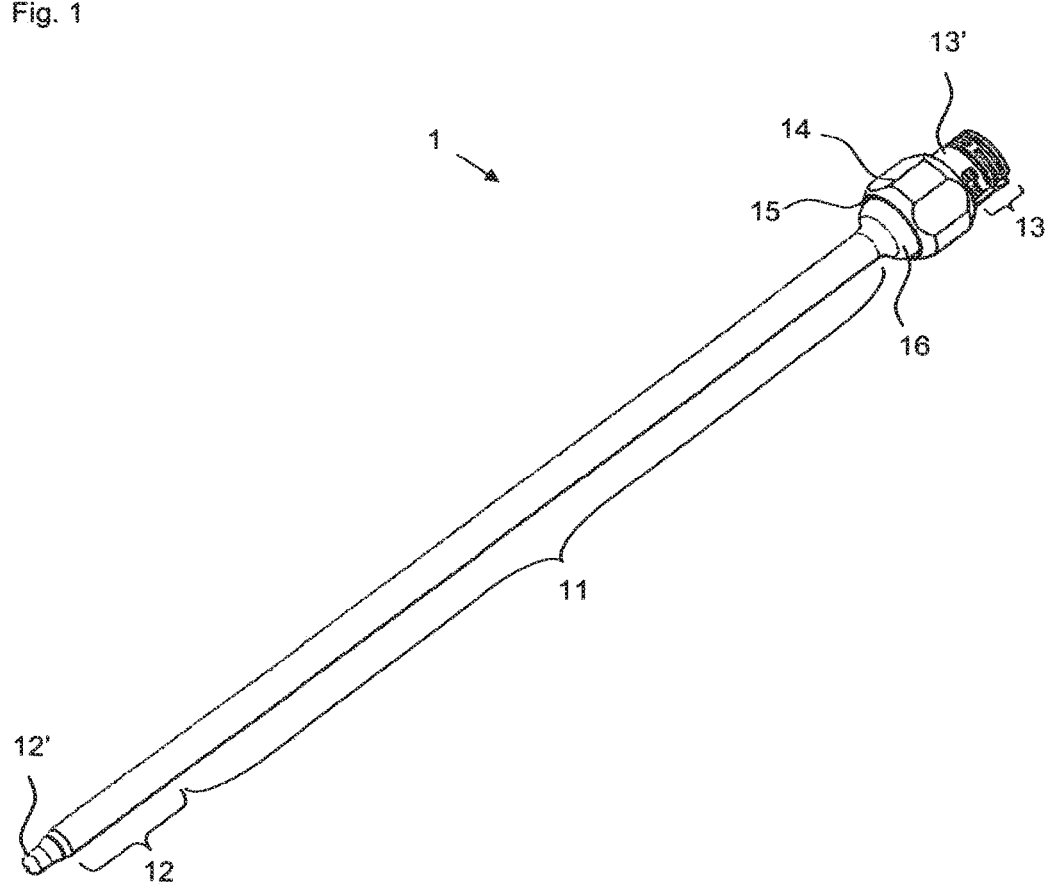
FIG. 1 shows a perspective view of the covering.

The covering 1 depicted in FIG. 1 has three sections 11, 12, 13: a proximal coupling section 13, a central shank section 11 and a distal expansion section 12. The covering 1 can be pulled over an elongate dilation tool 3 (see FIG. 10)

like a hood; to this end, the covering 1 is open from the coupling section 13 to the tip, i.e. the expansion section 12. In the coupling section 13, the tube of the shank section 11 has been pulled over a coupling sleeve 13' and adhesively bonded to the latter. The point of adhesion is in turn covered by a grip aid sleeve 14, which is adhesively bonded in a rotationally secured manner to the coupling sleeve 13' and additionally also held in an interlocking manner by an interaction between a latching recess and a latching lug (see FIG. 6). The tube consists of an elastic mesh material which can be stretched radially by the multiple of the rest diameter thereof without being plastically deformed or even destroyed; this becomes clear at the transition point 16: there, the tube is strongly dilated over a comparatively short longitudinal axial path such that it can be guided into the ring gap between coupling sleeve 13' and grip aid sleeve 14. At the distal end, the covering 1 comprises an end sleeve 12', which is pushed over the tip of the tube and adhesively bonded to the tube 11' or can also be crimped, like a wire end ferrule. The coupling section 13 serves to be able to couple the covering 1 reliably but nevertheless quickly to a dilation instrument. To this end, a bayonet closure element in the form of an L-shaped groove is present in the coupling section 13 (in this respect, see FIG. 4). At the most proximal end of the coupling section 13, a slit can be identified which provides a predetermined longitudinal axial elasticity in this section. In conjunction with a support face of the dilation instrument, this "structure-integrated spring" is pretensioned and used to secure the bayonet closure against inadvertent opening. The mesh material of the tube is so elastic that it can completely follow the expansion of the dilation tool without being damaged. Known coverings, which are only pulled over the expansion section of the dilation tool, for example silicone overcoats, disadvantageously slip off very easily during expansion and can, in the worst case scenario, be forgotten in the patient. The present invention renders it possible to couple the covering 1 in a permanent and secure manner to a dilation instrument since it extends over the complete length of the shank and is only connected to the dilation instrument on the handling section, as result of which a sufficient length is available for longitudinal axial stretching for compensating for the cross-sectional stretching in the expansion section. As a result, a uniform introduction of force into the tissue is made possible in mechanical dilation instruments. Mechanical dilation instruments generally have spreading jaws which expose gaps when opening such that, firstly, the pressure on the tissue increases and, secondly, the risk of trauma to the tissue by clamping is also increased. The covering 1 according to the invention prevents both effects without, however, having the known disadvantages in respect the fastening. Advantageously, it is even possible, under certain circumstances, to dispense with a dedicated restoring means of the dilation instrument when using the covering 1 according to the invention since the dimensions and the substance of the tube can be selected in such a way that a restoration force which also suffices for restoring the dilation instrument is generated. Preferably, the mesh material can consist of a fabric, braid or knit, in which the individual threads or wires are not connected to one another but can be freely displaced with respect to one another. An additional advantage of the covering 1 according to the invention consists of the essential components of the dilation instrument, namely the shank and the expansion section, no longer coming into direct contact with the tissue, but only the covering 1. After using the covering 1 during an operation, the covering 1 is simply disposed of, while the cleaning and disinfection outlay for the dilation instrument is significantly reduced.

Figure 2:
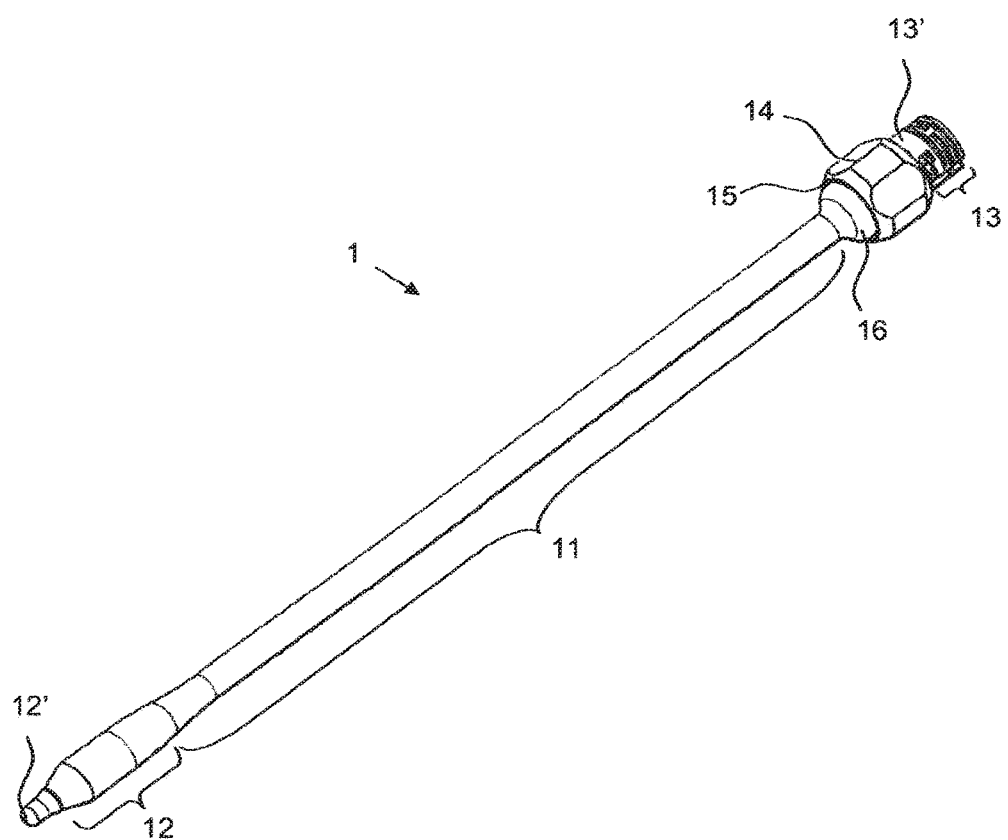
FIG. 2 shows a perspective view of the covering with a partially expanded expansion section.

FIG. 2 shows the covering 1 in a partly dilated state, with the dilation instrument itself not being shown. Here, the tip or the distal end sleeve 12' does not expand since it is adhesively bonded and/or crimped to the tube.

Figure 3:
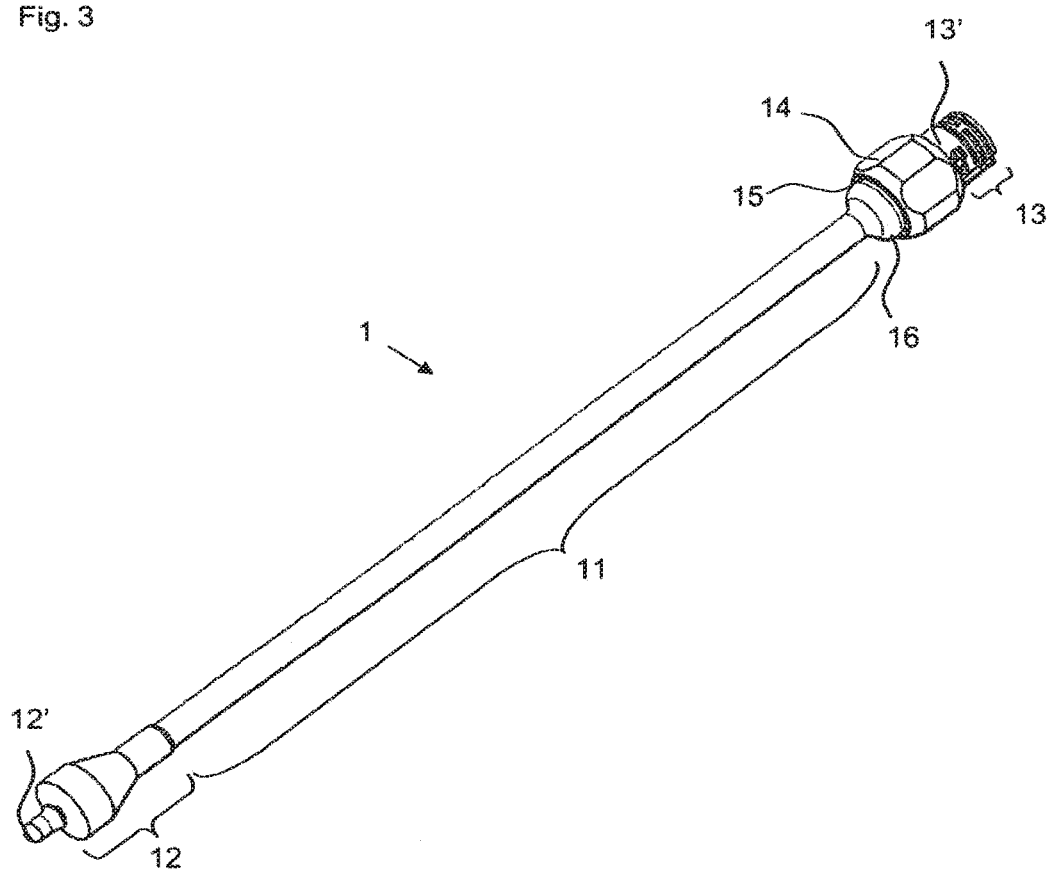
FIG. 3 shows a perspective view of the covering with a fully expanded expansion section.

FIG. 3 shows the state of the covering 1 in the case of a completely expanded expansion section 12. The mesh material elastically follows the expansion of the dilation instrument, i.e. it always returns to the state in FIG. 1 when the dilation instrument contracts. Naturally, the dilation instrument can also have a different expansion geometry since different expansion geometries are also used for different operation types. However, it is also always possible to use the same covering 1 for different dilation tools with different expansion geometries.

Figure 4:
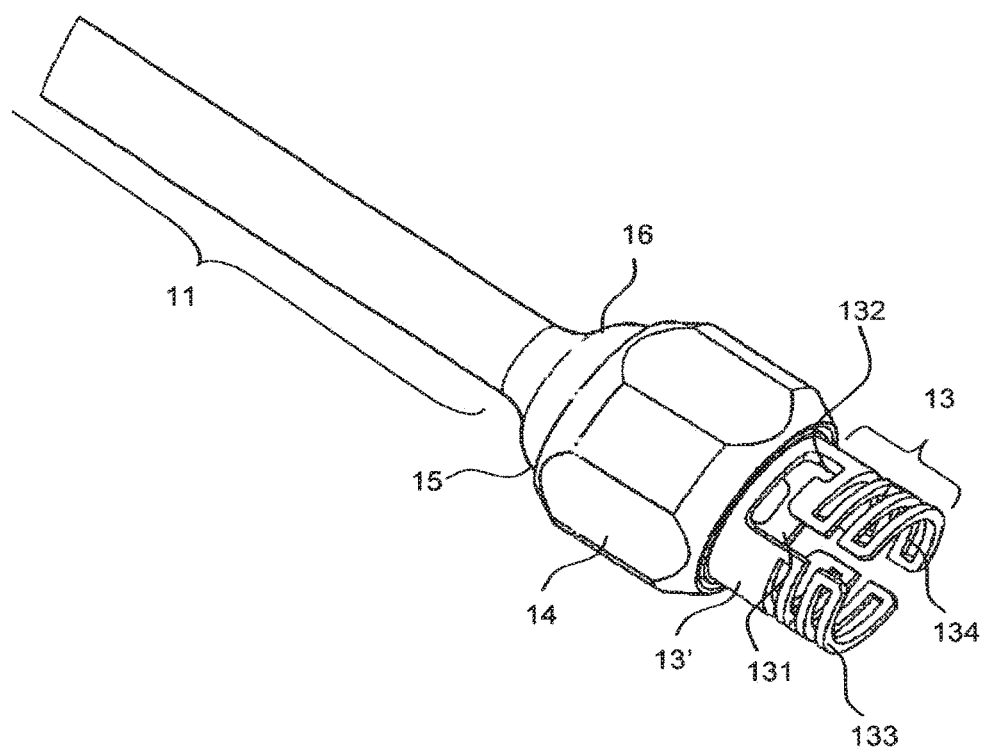
FIG. 4 shows a perspective partial view of the covering.

FIG. 4 shows the proximal end, i.e. the end facing the dilation instrument, of the covering 1, with part of the shank section 11 also being visible. In the region of the tube deflection 16, the tube is stretched radially from its rest diameter within a very short extent and finally pulled over the coupling sleeve 13'.

At its proximal end, the coupling section 13 has a plurality of circumferential slits 134, which respectively provide a longitudinal axial elasticity in this section. Overall, there are a total of 3 parallel rows of slits, with webs being arranged between the slits 133 but being offset in the circumferential direction such that they extend, as it were, in a rectangular function-like manner, as a result of which an increased overall elasticity is achieved. The webs 133 are respectively mirrored in a diameter plane containing the diameter and the longitudinal axis on the opposite longitudinal quarter. The bayonet closure element is formed by an L-shaped insertion groove 131 which extends parallel to the longitudinal axis and has a locking recess 132 at the closed end, in which locking recess, in the locked state, the locking lug of the coupling device of the dilation tool engages. Here, the resilient section with the slits 134 ensures that the locking lug cannot simply slip out of the locking recess 132 again by rotation, but that it can only slip out if the resilient force is overcome by longitudinal axial pressure.

Figure 5:
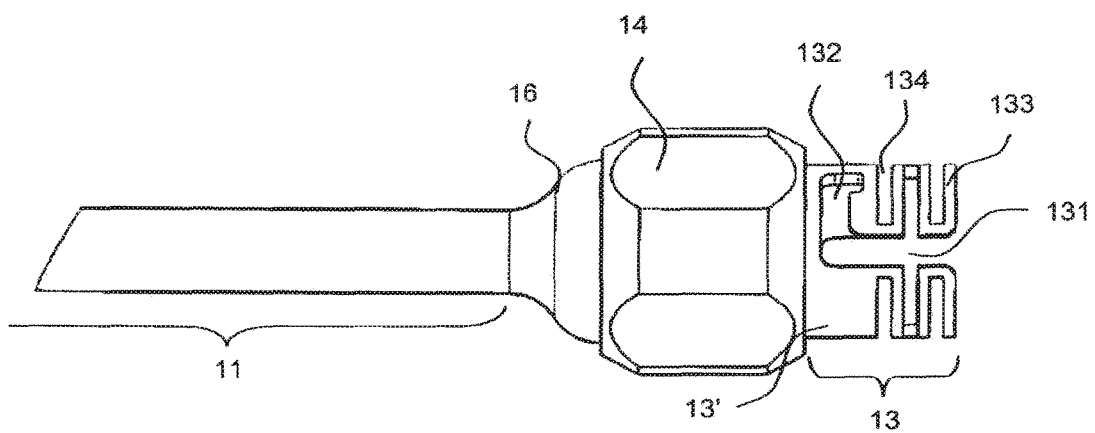
FIG. 5 shows a top view of part of the covering.

FIG. 5 shows the section of the covering 1 from FIG. 4 in a lateral view, wherein the embodiment once again allows good identification of the resilient section of the coupling section 13 with slits 134 and webs 133 extending in a rectangular function-like manner. The grip aid sleeve 14 has gripping areas 14, which can both be gripped by a key and enable comfortable manual rotation.

Figure 6:
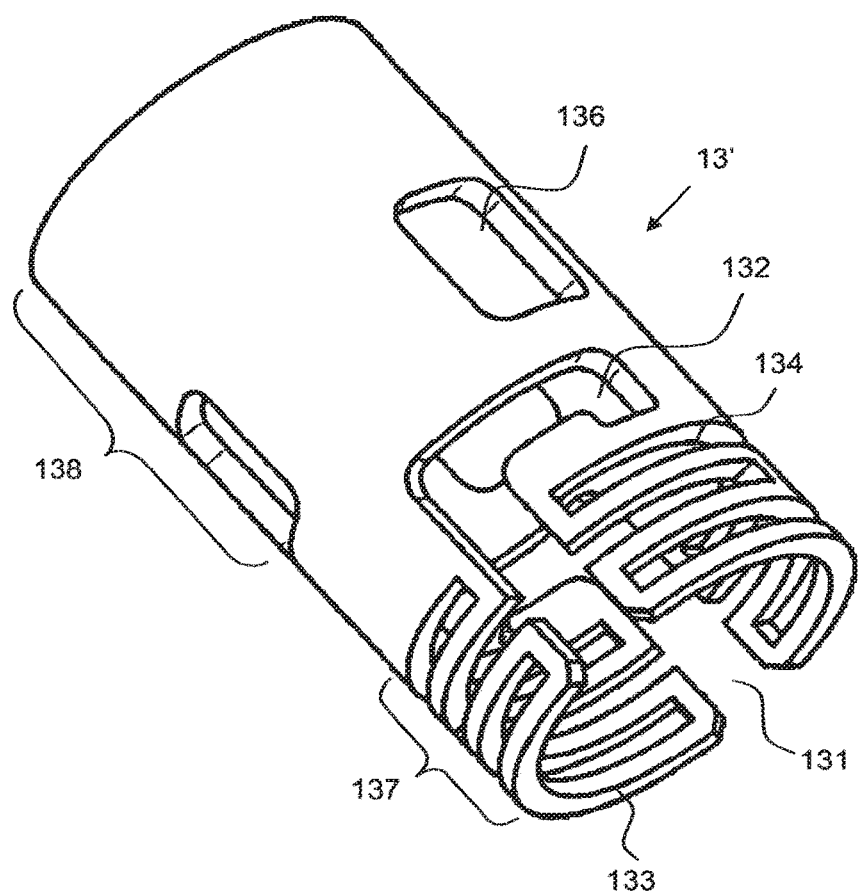
FIG. 6 shows a perspective view of the coupling sleeve.

FIG. 6 merely depicts the coupling sleeve 13' in a perspective manner. The resilient function achieved by slitting is implemented in the proximal end section 137, through which the slits 134 also extend in parallel, partly circumferentially and normally with respect to the longitudinal axis. The distal end section 138 is the section of the coupling sleeve 13' over which the tube-like shank section of the covering 1 (see FIG. 1) is pulled and over which the grip aid sleeve 14 (see FIG. 5) is also arranged. In the region of the distal end section 138, three latching recesses 136, which are arranged distributed at the same angle over the circumference, can be identified, with which latching lugs of the grip aid sleeve 14 (see FIG. 5) can be brought into engagement such that the transmission of the torque from the grip aid sleeve to the coupling sleeve 13' can also in part be brought about in an interlocking manner, which is advantageous since, as a result of this, the mesh material is not strained by relative movements in the ring gap between the coupling sleeve 13' and the grip aid sleeve 14 (see FIG. 5).

Figure 7:
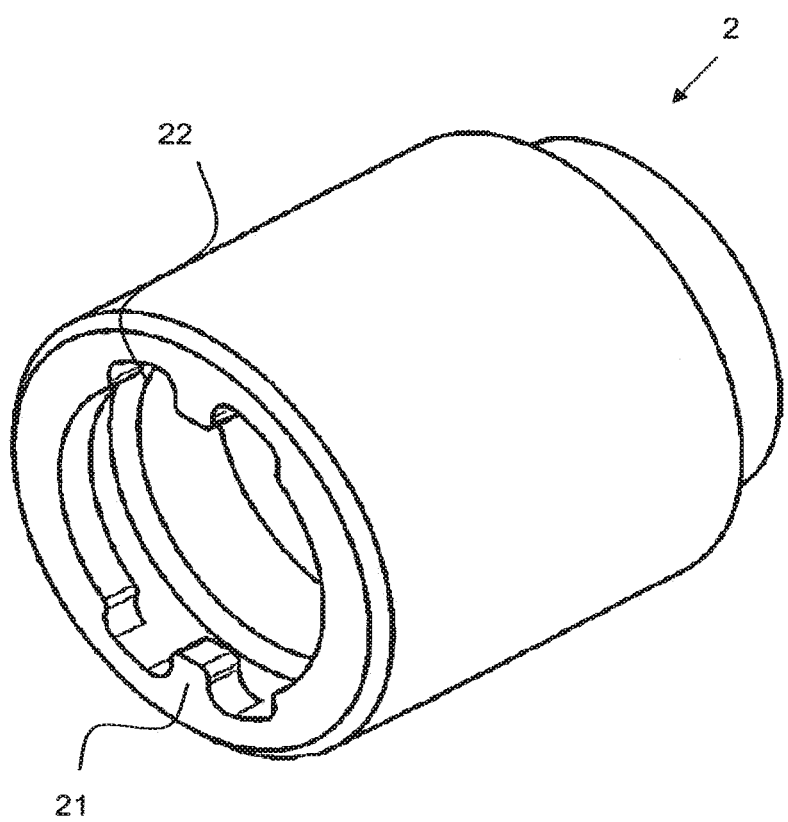
FIG. 7 shows a perspective view of the coupling device.
Figure 8:
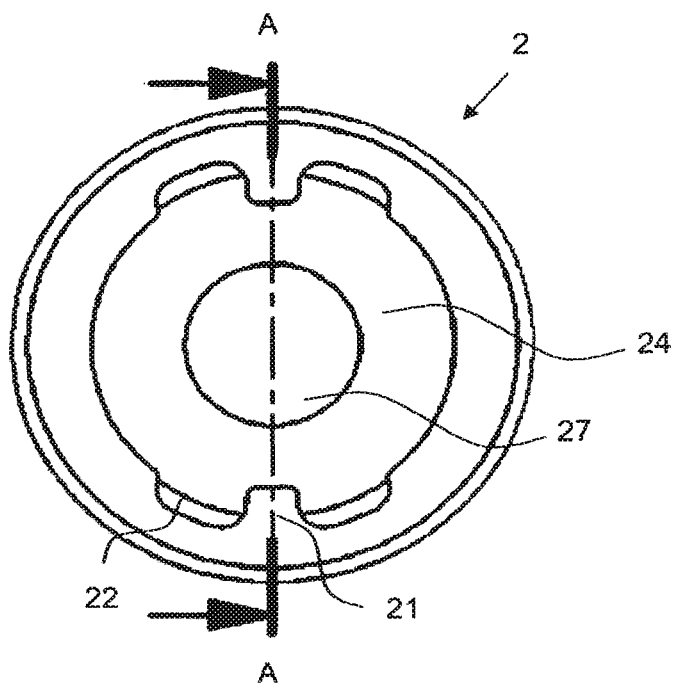
FIG. 8 shows a top view of the coupling device.
Figure 9:
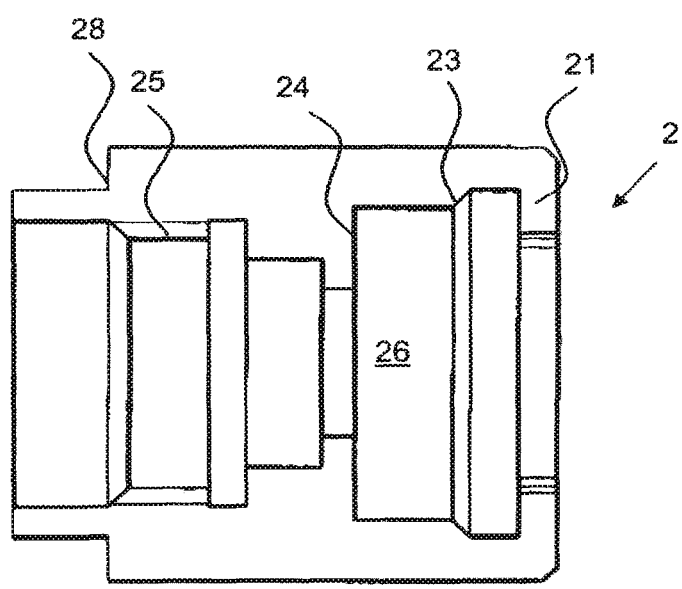
FIG. 9 shows a longitudinal section of the coupling device.

FIG. 7 to FIG. 9 show the coupling device 2, which also has a sleeve shape, and into which the coupling sleeve 13' (see FIG. 6) is partly inserted along the longitudinal axis thereof. The locking lugs 21 of the coupling device 2 are provided to be inserted into the L-shaped insertion groove of the coupling sleeve 13' (see FIG. 6) and to be moved up to the closed end thereof. The dimensions of the locking lugs 21 correspond to the dimensions of the insertion groove 131 and of the locking recess 132 of the coupling sleeve 13' (see FIG. 6). Along the proximal end section thereof, in which the longitudinal axial elasticity is provided, the coupling sleeve is inserted into the coupling device 2, with the proximal end section of the coupling sleeve then being held in the holding space 26 of the coupling device 2. The recesses 22, which are present on both sides of the two locking lugs 21, are for the manufacture of the locking lugs 21. In the top view of FIG. 8, a passage opening 27 can moreover be identified, through which the shank of the dilation instrument containing the actuation mechanism is guided. Naturally, the dilation instrument can also have a different type of actuation such that, for example, hydraulic lines, pneumatic lines and/or electrical lines can also be guided through the passage opening 27. Furthermore, a sectional plane A-A is also plotted, with this longitudinal section being shown in FIG. 9. A female thread 25, with which the coupling device 2 is screwed to the dilation instrument, can be identified in the longitudinal section. Furthermore, it is also possible to see that a cylindrical section with a larger diameter distally (i.e. further to the right-hand side in this case) adjoins the holding space 26 for the proximal end section of the coupling sleeve 13' (see FIG. 6), wherein an insertion chamfer or an insertion bevel 23, which should ease the insertion of the coupling sleeve into the holding space 26, is arranged therebetween. At the proximal end thereof (see the left-hand side in the figure), the coupling device 2 has a section with a smaller diameter and a shoulder 28 which is provided to lie flush on an opposite area of a distal end of the dilation instrument. Provision can be made for the proximal end section with the smaller diameter to be held in a cylindrical bore of the dilation instrument and for the larger external diameter to correspond to the external diameter of the dilation instrument since this can achieve a harmonious general view of the overall instrument with a coupled coupling section. A colored ring for encoding the instrument or the strength, charge or another property thereof, can be attached to the shoulder 28.

Figure 10:
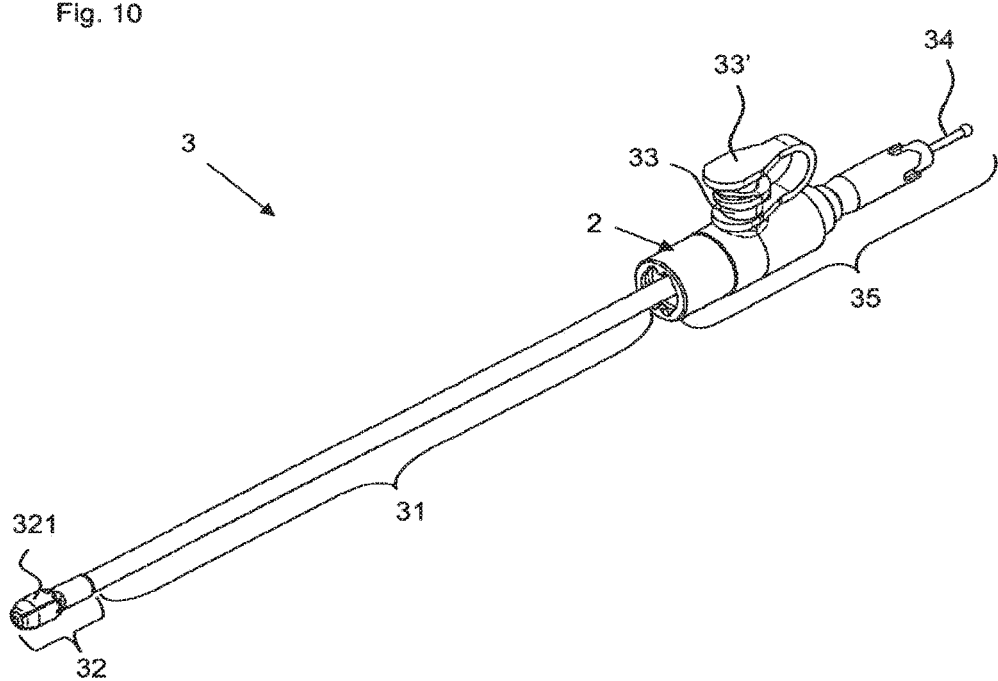
FIG. 10 shows a perspective view of the dilation tool without a covering.

Such a dilation instrument 3 with a coupled-on coupling device 2 is depicted in FIG. 10. The instrument 3 can be subdivided into three sections 31, 32, 35: a handling section 35, a shank section 31 and an expansion section 32. A force transmission element with an end-sided actuation knob 34 is arranged at the proximal end of the handling section 35, which force transmission element has a functional connection to the expansion section 32, for example by means of a Bowden cable or a pushing/pulling rod guided in the interior of the shank 31. By pulling out the knob 34, the spreading jaws 321 are actuated by means of the pushing rod, whereupon the spreading jaws 321 expand in the radial direction. The coupling device 2 is screwed or adhesively bonded to the distal end of the handling section 35, wherein the external diameters of the coupling device 2 and of the handling section 35 are approximately equal such that this results in a harmonious transition which is comfortable from an ergonomic point of view. Prior to carrying out an operation with the dilation instrument 3, a covering according to the invention (see FIG. 1) is pulled over the expansion section 32 and the shank 31. The coupling sleeve 13' with the resilient proximal end section of the covering 1 (see FIG. 1) is threaded with the insertion groove being in the locking lugs of the coupling device 2 and, after a pretension of the resilient section is generated, rotated to the locking recess of the coupling sleeve. After releasing the coupling sleeve, the covering is secured by the interaction of the pretension of the resilient section of the coupling sleeve with the locking recess and the locking lug and can no longer inadvertently slip from the dilation instrument. In the coupled state, the covering completely covers the shank 31 and the expansion section 32 of the dilation instrument. Advantageously, the mesh material of the covering is so elastic that it can follow the expansion of the expansion section of the dilation instrument 3 and can even also exert a restoration force on the spreading jaws 321. A dilation instrument 3 with a covering pulled thereover can be cleaned and disinfected in clinical daily use with very little outlay after the operation, since it is not the actual instrument but only the covering which comes into contact with the patient tissue.

Figure 11:
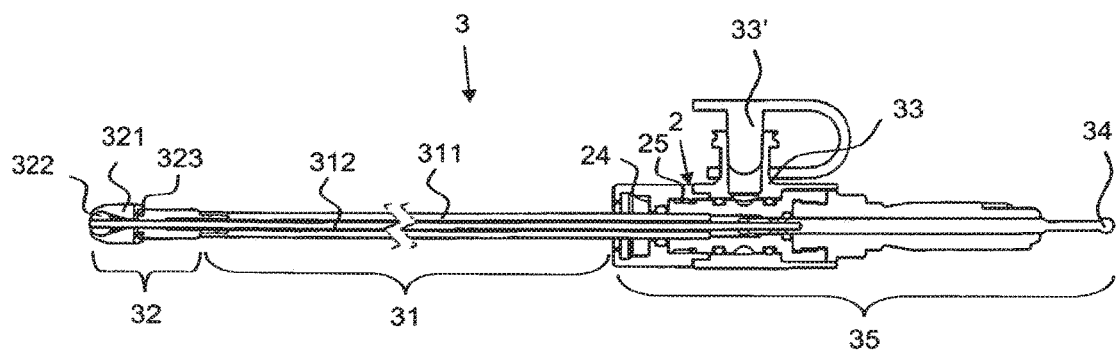
FIG. 11 shows a longitudinal section of the dilation tool without a covering.

The function of the actuation mechanism of the dilation instrument 3 is briefly explained on the basis of FIG. 11. A pulling rod 312, which is guided in a sheath 312, extends in the interior of the shank section 31. The pulling rod 312 extends from the expansion section 32 to the outermost distal end of the handling section 35, where it has a knob 34. At the knob 34, the pulling rod 312 can be directly actuated by hand, or an actuation aid device, for example with a forceps or pistol grip, can be brought into engagement therewith. Spreading jaws 321, which are hinged on the fulcrum 323, can be identified in the expansion section 32. In this longitudinal sectional view, substantially only two spreading jaws 321, which can move in the plane of the image, can be identified; however, the instrument has further spreading jaws distributed over the circumference, which enable a three-dimensional dilating of the expansion section 32. In the expansion section 32, a sphere 322 is attached at the distal end of the pulling rod 312, which sphere is displaced relative to the spreading jaws 322 when actuated and slides down an angled trajectory of the spreading jaws 321, as a result of which the spreading jaws are pressed apart. Furthermore, a feed port 33 is arranged in the handling section 35, by means of which liquid or gaseous media for rinsing or cleaning the dilation instrument 3 can be supplied. A cap 33' which is fastened by a clip such that it cannot be lost is used to seal the feed port 33 such that no foreign bodies can enter during operation.

Figure 12:
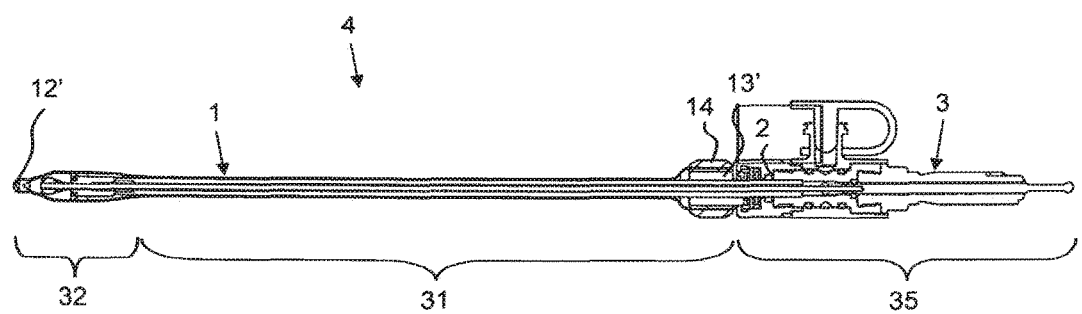
FIG. 12 shows longitudinal section of the dilation tool with a covering.
Figure 13:
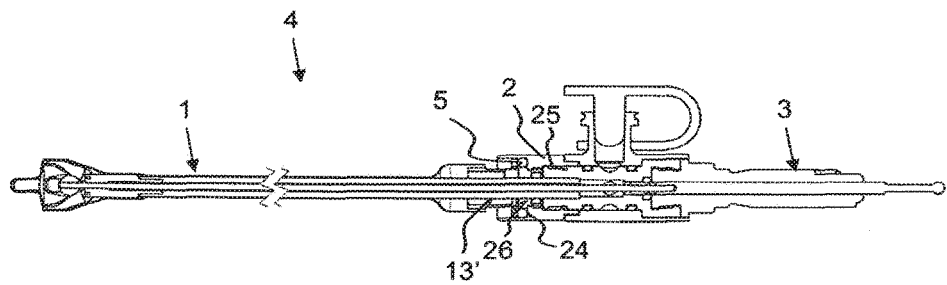
FIG. 13 shows a longitudinal section of a different dilation tool with a covering.

FIG. 12 depicts, in a longitudinal section, the dilation instrument 3 shown in FIG. 11 with a coupled covering; therefore, this is the dilation device 4 according to the invention. The covering 1 is, by means of the coupling sleeve 13', detachably coupled to the coupling device 2, which in turn is connected in a detachable manner to the distal end of the handling section 35 of the dilation instrument 3. The covering 1 extends in a tube-like manner and with a tight fit along the whole shank section 31 of the dilation instrument 3 and also over the expansion section 32. At the outermost distal end of the dilation device 4, the covering is closed off by the end sleeve 12'. The covering 1 can always follow an expansion of the expansion section 32 with a tight fit due to the mesh structure and good elasticity of said covering. The state of the dilation device with a completely expanded expansion section 32 is depicted in FIG. 13.

As an alternative to the resilient proximal end section of the coupling sleeve 13', the coupling sleeve 13' can also be rigid over the complete length thereof, wherein the desired resilient function is achieved by an additional component. Such an embodiment is depicted in FIG. 13. Here, an O-ring 5, which provides the elasticity which presses the locking lug of the coupling device into the locking recess of the coupling sleeve, is arranged between the support end face 24, the coupling device 2 and the opposite distal support face of the coupling sleeve 13'. However, it is also possible to use other resilient components, for example a spring, in particular a helical spring, or a gas filling; however, this is not shown figuratively. In this embodiment, the coupling device 2 is also connected in a detachable manner by means of a thread 25 to the distal end of the handling section 35 (see FIG. 12) of the dilation device 3 and the coupling sleeve 13' is partly held by the holding space 26. The embodiment with O-ring 5 instead of resilient coupling sleeve 13' is advantageous in that the covering 1 can be provided in a more cost-effective manner; there is no need for a complex slit structure to be manufactured; rather use is only made of a standardized O-ring 5.

Figure 14:
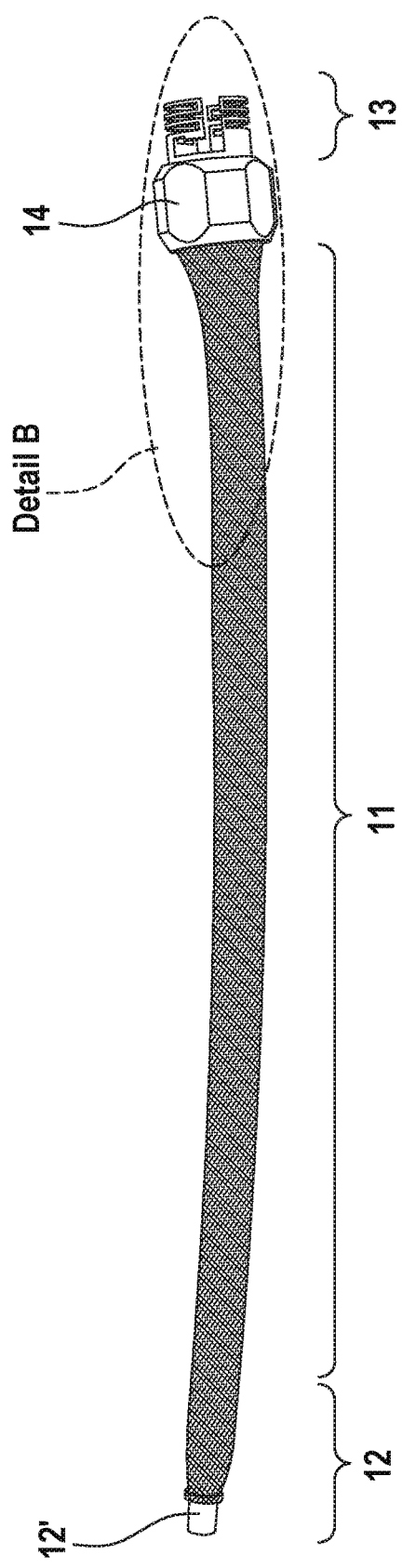
FIG. 14 shows a further top view of a covering.
Figure 15:
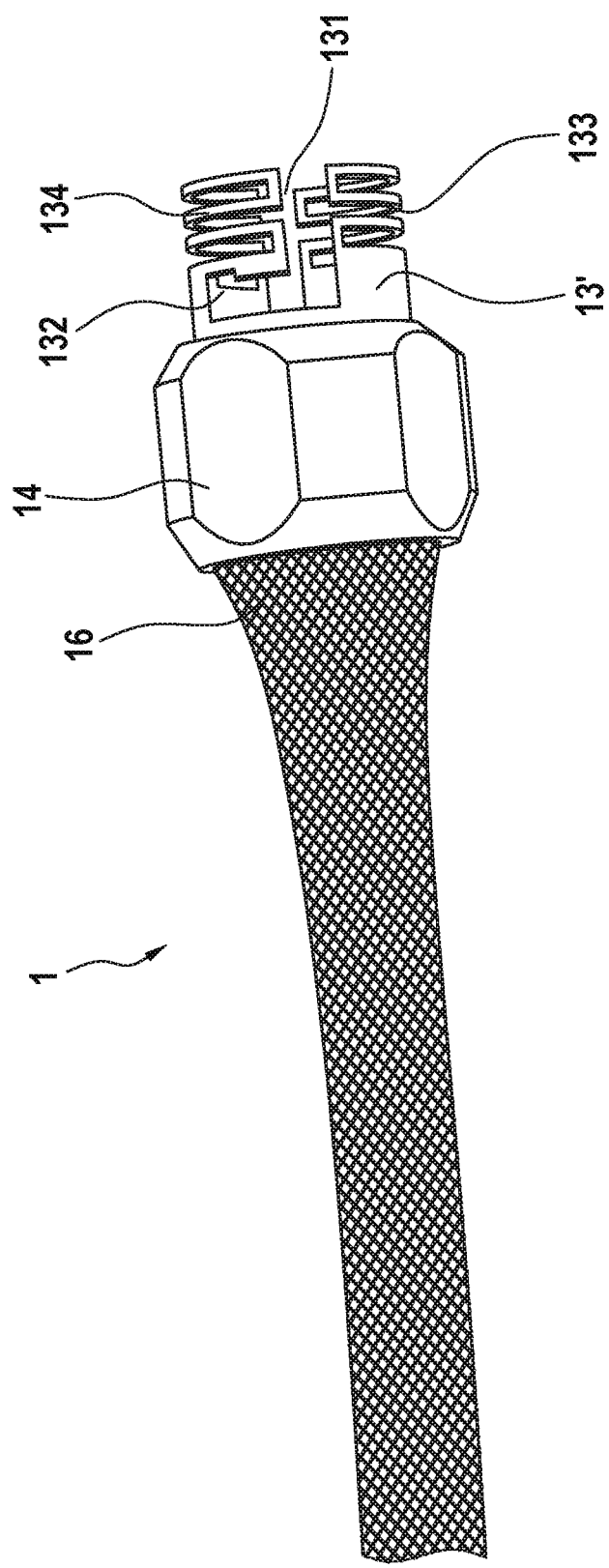
FIG. 15 shows a top view of detail B in FIG. 14.

FIG. 14 and FIG. 15 depict a further top view of the covering 1 according to the invention, wherein f shows detail B from FIG. 14. Here, it is easy to identify the mesh structure in the shank section 11. The spanner faces of the grip aid sleeve 14 and the insertion groove 131, the locking recess 132 and the elements of the resilient section—slits 134 and webs 133—are also depicted.

LIST OF REFERENCE SIGNS

| Number | Description |
| --- | --- |
| 1 | Covering for a dilation instrument |
| 11 | Shank section of the covering |
| 12 | Distal expansion section of the covering\ |
| 12' | End sleeve of the covering |
| 13 | Proximal coupling section of the covering |
| 13' | Coupling sleeve |
| 131 | Insertion recess in the coupling sleeve |
| 132 | Locking recess in the coupling sleeve |
| 133 | Web of the coupling sleeve |
| 134 | Slit of the coupling sleeve |
| 136 | Latching recess in the coupling sleeve |
| 137 | Proximal end section of the coupling sleeve |
| 138 | Distal end section of the coupling sleeve |
| 14 | Grip aid sleeve |
| 15 | Ring gap between grip aid sleeve and coupling sleeve |
| 16 | Tube deflection |
| 2 | Coupling device of the dilation instrument |
| 21 | Locking lug of the coupling device |
| 22 | Recess for assembly tools in the coupling device |
| 23 | Insertion chamfer of the coupling device |
| 24 | Proximal support end face of the coupling device |
| 25 | Female thread of the coupling device |
| 26 | Holding space of the coupling device |
| 27 | Passage opening in the coupling device |
| 28 | Proximal shoulder of the coupling sleeve |
| 3 | Dilation instrument |
| 31 | Shank of the dilation instrument |
| 32 | Expansion section of the dilation instrument |
| 321 | Spreading jaws of the dilation instrument |
| 33 | Feed port of the dilation instrument |
| 33' | Cover with loop of the feed port |
| 34 | Force transmission element |
| 35 | Handling section of the dilation instrument |
| 4 | Dilation device |
| 5 | O-ring |

The invention claimed is:

1. A dilation device comprising
a dilation instrument which comprises a distal radially expandable section which is coupled via an elongate shank to a handling section, the expandable section adapted to expand in two directions perpendicular to each other and orthogonal to the elongate shank,
an expandable covering, with a closed distal end and an open proximal end, for the expandable section of the dilation instrument,
a coupling device connected to a distal end of the handling section of the dilation instrument, the coupling device having at least one radially inwardly extending locking lug,
a coupling sleeve having a bayonet closure element, wherein there is a locking recess at a closed end of an insertion recess, characterized in that the covering has a shank section extending along the shank of the dilation instrument, wherein the open proximal end of the covering is detachably coupled to the distal end of the handling section of the dilation instrument,
the coupling sleeve is longitudinally axially elastic with a plurality of parallel slits aligned normally with respect to the longitudinal axis with webs between the slits, and
in a locked state, the locking lug is held by the locking recess of the coupling sleeve such that the coupling sleeve secures the expandable covering to the dilation instrument.

2. The dilation device according to claim 1, characterized in that
the covering consists of wire mesh.

3. The dilation device according to claim 1, characterized in that
the shank section of the covering is connected at the open proximal end to the coupling sleeve,
wherein the coupling sleeve of the covering is detachably coupled to the coupling device of the dilation instrument.

4. The dilation device according to claim 3, characterized in that
the coupling device comprises a holding space for the coupling sleeve of the covering, which holding space extends in a longitudinal axial manner from a distal end face of the coupling device in the direction of the proximal end, wherein the coupling sleeve is held therein, at least along a proximal end section, and wherein a support end face, on which the coupling sleeve is supported, adjoins the holding space in the proximal direction.

5. The dilation device according to claim 3, characterized in that
at least one radially outwardly extending assembly recess is present on the coupling device, adjacent in the circumferential direction to at least one locking lug, and
the coupling device has an insertion chamfer at a distal end of a holding space.

6. The dilation device according to claim 1, characterized in that
the dilation instrument is actuated using hydraulic, pneumatic, or electrical lines.

7. An expandable covering for a distal expansion section of a dilation instrument,
wherein the covering has a closed distal end and an open proximal end for detachably coupling to a dilation instrument, characterized in that the covering consists of a wire mesh material and has a shank section, which is connected to a coupling sleeve at the open proximal end, the coupling sleeve has a bayonet closure element and in a locked state the coupling sleeve secures the covering to the dilation instrument, the coupling sleeve is longitudinally axially elastic with a plurality of parallel slits aligned normally with respect to the longitudinal axis with webs between the slits, and the distal expansion section is adapted to expand in two directions perpendicular to each other and orthogonal to the shank section.

8. The expandable covering according to claim 7, characterized in that, in the proximal end section, there being webs between the slits, wherein the coupling sleeve has at least two ring sectors, and wherein the webs are respectively arranged in a mirrored fashion in neighboring ring sectors.

9. The expandable covering according to claim 7, characterized in that a grip aid sleeve is arranged over a distal end section of the coupling sleeve, with a spanner engagement portion or knurling, which is connected in a rotationally secured manner to the distal end section.

10. The expandable covering according to claim 9, characterized in that the coupling sleeve comprises a latching recess in a wall, and the grip aid sleeve comprises a latching lug, wherein the latching lug of the grip aid sleeve engages with the latching recess of the coupling sleeve.

11. The expandable covering according to claim 7, further comprising an end sleeve, which is arranged over the distal closed end of the covering.

12. The expandable covering according to claim 7, characterized in that the mesh material is a knit or braid.

13. The expandable covering according to claim 7, characterized in that the substance of the mesh material has a diameter of 0.08 mm.

14. The expandable covering according to claim 7, characterized in that the substance of the mesh material is a biocompatible stainless steel.

15. The expandable covering according to claim 7, characterized in that the substance of the mesh material is a shape memory alloy.

16. A dilation device comprising a dilation instrument which comprises a distal expandable section which is coupled via an elongate shank to a handling section, the expandable section adapted to expand in two directions perpendicular to each other and orthogonal to the elongate shank, and an expandable covering, with a closed distal end and an open proximal end, for the expandable section of the dilation instrument, characterized in that the covering has a shank section extending along the shank of the dilation instrument, wherein the open proximal end of the covering is detachably coupled to a distal end of the handling section of the dilation instrument;

a coupling sleeve is longitudinally axially elastic in a proximal end section having a plurality of parallel slits aligned normally with respect to the longitudinal axis, with there being webs between the slits, wherein the coupling sleeve has at least two ring sectors, and wherein the webs are respectively arranged in a mirrored fashion in neighboring ring sectors;

the coupling sleeve has a bayonet closure element and in a locked state the coupling sleeve secures the expandable covering to the dilation instrument.

17. A dilation device comprising:

a dilation instrument having a distal expandable section coupled via an elongate shank to a handling section, the expandable section expanding in at least two directions perpendicular to each other and orthogonal to the elongate shank;

an expandable covering of wire mesh for the expandable section of the dilation instrument, the expandable covering having a closed distal end and an open proximal end;

a coupling sleeve at the open proximal end of the expandable covering, the coupling sleeve longitudinally axially elastic in a proximal end section and having a plurality of parallel slits aligned normally with respect to the longitudinal axis with webs between the slits;

a coupling device at the distal end of the handling section of the dilation instrument, the coupling device detachably coupled to the coupling sleeve of the expandable covering;

the coupling sleeve having a locking recess at a closed end of an insertion recess, and the coupling device having at least one radially inwardly extending locking lug with dimensions that correspond to the insertion recess such that in a locked state the locking lug is held by the locking recess and the coupling sleeve secures the expandable covering to the dilation instrument.

18. The dilation device according to claim 17, the coupling device having a holding space for the coupling sleeve of the expandable covering, which holding space extends in a longitudinal axial manner from a distal end face of the coupling device in the direction of the proximal end, wherein the coupling sleeve is held therein, at least along a proximal end section, and wherein a support end face, on which the coupling sleeve is supported, adjoins the holding space in the proximal direction.

19. A dilation device comprising a dilation instrument having a distal radially expandable section which is coupled via an elongate shank to a handling section, the expandable section adapted to expand in two directions perpendicular to each other and orthogonal to the elongate shank, an expandable covering for the expandable section of the dilation instrument, the expandable covering having a closed distal end and an open proximal end, a coupling device connected to a distal end of the handling section of the dilation instrument, the coupling device having at least one radially inwardly extending locking lug, a coupling sleeve having a bayonet closure element formed by an L-shaped insertion groove, the coupling sleeve also having a locking recess at a closed end of an insertion recess, wherein the covering has a shank section extending along the shank of the dilation instrument, and the open proximal end of the covering is detachably coupled to the distal end of the handling section of the dilation instrument, in the proximal end section, the coupling sleeve is longitudinally axially elastic with a plurality of parallel slits aligned normally with respect to the longitudinal axis with webs between the slits, and in a locked state, the locking lug is held by the locking recess of the coupling sleeve such that the coupling sleeve secures the expandable covering to the dilation instrument.

* * * * *